US008137642B2

(12) United States Patent
Hutchins et al.

(10) Patent No.: US 8,137,642 B2
(45) Date of Patent: Mar. 20, 2012

(54) METHOD AND APPARATUS FOR CALIBRATING FILTERS DURING SPECIMEN COLLECTION

(75) Inventors: Timothy Hutchins, Attleboro Falls, MA (US); Steven Scampini, Groton, MA (US); Eric Baur, Marlborough, MA (US)

(73) Assignee: Cytyc Corporation, Marlborough, MA (US)

( * ) Notice: Subject to any disclaimer, the term of this patent is extended or adjusted under 35 U.S.C. 154(b) by 320 days.

(21) Appl. No.: 12/482,731

(22) Filed: Jun. 11, 2009

(65) Prior Publication Data

US 2009/0312955 A1 Dec. 17, 2009

Related U.S. Application Data

(60) Provisional application No. 61/061,518, filed on Jun. 13, 2008.

(51) Int. Cl.
*G01D 18/00* (2006.01)
(52) U.S. Cl. ............... 422/536; 95/45; 73/1.01; 73/1.02
(58) Field of Classification Search .................. 422/536; 95/45; 73/1.01, 1.02
See application file for complete search history.

(56) References Cited

U.S. PATENT DOCUMENTS

| 6,913,921 B2 | 7/2005 | Fischer |
| 2008/0081363 A1 | 4/2008 | Hutchins et al. |

OTHER PUBLICATIONS

Technical Brief, Microfluor® II Filter Cartridge Integrity Testing, pp. 1-8, 2004.*
Southern Metal Processing, Metal Cleaning for Industry, pp. 1-4 (2007).*

* cited by examiner

*Primary Examiner* — Jill Warden
*Assistant Examiner* — Monique Cole
(74) *Attorney, Agent, or Firm* — Vista IP Law Group LLP

(57) ABSTRACT

A bubble point of a combination of a filter and a liquid is calibrated by applying an initial back pressure through the filter toward the liquid; taking a first plurality of measurements of the level of the liquid in the container; calculating a first variance of the first plurality of measurements; and comparing the first calculated variance with a known threshold variance. Then a second plurality of measurements of the level of the liquid in the container is taken; a second variance of the second plurality of measurements is calculated; and the second calculated variance is compared with a known threshold variance. The above described steps are repeated at incrementally increased back pressures until the first and second calculated variances are each greater than or equal to the known threshold variance, which is about 0.01. The bubble point is determined to be the back pressure at that point. If the determined bubble point is less than or equal to the known threshold bubble point, which is about 0.8 pounds per square inch, the filter is identified as unsuitable for use in cell block formation.

9 Claims, 5 Drawing Sheets

METHOD AND APPARATUS FOR CALIBRATING FILTERS DURING SPECIMEN COLLECTION

RELATED APPLICATION DATA

The present application claims the benefit under 35 U.S.C. §119 to U.S. provisional patent application Ser. No. 61/061,518, filed Jun. 13, 2008. The foregoing application is hereby incorporated by reference into the present application in its entirety.

FIELD OF THE INVENTION

The present inventions pertain to methods for preparing cells for microscopic examination, and more particularly to automated and semi-automated methods for embedding cellular materials and tissue fragments within a paraffin substrate that may be thereafter thinly-cut using a standard microtome for microscope examination.

BACKGROUND

It is useful for diagnosing or detecting a disease process to perform a histologic or cytologic examination of a tissue cell sample using a light microscope. This requires that a tissue (cellular material) sample must first be retrieved from the patient, and then processed for microscopic examination. A number of minimally invasive techniques are available for retrieving and collecting cell samples from a patient, e.g., by using a fine needle aspiration biopsy, or by brushing body cavity surfaces accessible through minimally invasive endoscopic techniques. A variety of cell sample processing techniques are also known, such as the Cytospin® technique and the Thin-prep® technique, for depositing cellular materials and tissue fragments directly onto a microscope slide. Another technique, commonly referred to as a cell block preparation, immobilizes cellular materials and/or small tissue fragments within a solid support structure, typically paraffin, to form a "cell block". Thin sections of the cell block are then cut with a microtome and mounted onto a microscope slide for examination.

U.S. Pat. No. 6,913,921 ("the '921 patent") discloses and describes methods and apparatus for cell block preparation, including providing a tissue collection cassette that serves a dual function of capturing cellular sample matter and providing a fluid pathway through which the cell processing and embedding reagents can flow. The cellular sample material is provided in an aqueous solution or a liquid cell preservative, which is passed through the tissue cassette across a filter that traps the cells and tissue fragments. A reagent flow pathway is configured to sequentially pass embedding reagents (alcohol, xylene, eosin stain) and liquefied paraffin through the tissue cassette and the cell sample already deposited on the filter. Once the paraffin is cooled, the filter is peeled away, leaving a paraffin "disk" protruding from the tissue cassette with embedded cellular matter positioned at the end of the disk in a plane at which a tissue section can be cut using a standard microtome for microscope examination. U.S. patent application Ser. No. 11/839,531, filed on Aug. 15, 2007, and assigned to the assignee of the present invention ("the '531 application"), discloses a substantially automated cell block creation that does not require human oversight during creation, including a two-piece cassette and filter assembly, to achieve more consistent cellular matter quantities in the created cell blocks, shorter processing time, reduced use of hazardous reagents, and more fully encapsulated cell blocks to preserve nucleic acid integrity. The contents of the respective '921 patent and '531 application are hereby fully incorporated by reference as if fully set forth herein.

When dispensing sample fluid into collection wells in the disclosed processes of the '531 application, certain samples will tend to clog the filter before a sufficient cellular material layer is retained. Such samples usually contain small individual cells, such as lymphocytes and other inflammatory cells, which have a tendency to stack and almost immediately impede the fluid flow across the filter. In order to collect additional cellular materials, and therefore a larger cell layer retained by the filter, air bubbles are pushed (or pulsed) through the filter from the waste chamber to temporarily lift the cellular materials away from the filter surface, and allow more liquid to pass through. This is done by applying a pressure within the waste chamber just larger than the bubble point of the filter and sample liquid combination to gently lift the cellular material from the filter surface. When sample collection has stalled, this small pressure pulse can lift the sample from the filter and allow more sample to be collected.

The bubble point is the pressure required on one side of a filter to produce bubbles on the other side of the filter, which is in contact with a liquid. The bubble point varies depending on the pore size of the filter and the surface tension of the liquid with which the filter is in contact. The bubble point of a filter can be manually calibrated by incrementally increasing the pressure applied to the non-liquid side of the filter ("back pressure") and visually observing when bubbles first form. The back pressure at which bubbles first form is the bubble point of the filter and liquid combination.

In the disclosed processes of the '531 application, the bubble point of the filter and sample liquid combination is known to the user prior to initiating cell block creation. If the pressure applied is lower than the bubble point, the impeding cellular materials will not be sufficiently lifted away from the filter surface to allow for efficient sample processing. If the pressure applied is exceeds the bubble point by a large amount, the impeding cellular materials may be ejected from the sample well of the cassette. This may lead to loss of valuable sample and may also occlude equipment mounted above the sample well, such as an ultrasonic liquid level sensor, resulting in spurious level detection. Thus, while representing an improvement over the then-state of the art for cell block preparation, the methods and apparatuses disclosed in the '921 patent and the '531 application require using a pre-calibrated filter with a known bubble point to determine the appropriate back pressure to dislodge impeding cellular material without ejecting it from the sample well of a cassette.

SUMMARY OF THE DISCLOSED INVENTIONS

Methods and apparatus are disclosed herein for the efficient creation of paraffin-embedded cell blocks, including (but not limited to) automated calibration of a bubble point of a filter and liquid combination and automated detection of "out of spec" or compromised filters, both of which prevent loss of valuable samples.

In one embodiment, a method of calibrating a bubble point of a combination of a filter and a liquid includes dispensing the liquid into a container, a surface of which is formed by the filter in contact with the liquid; applying an initial back pressure through the filter toward the liquid; taking a first plurality of measurements of the level of the liquid in the container; calculating a first variance of the first plurality of measurements; and comparing the first calculated variance with a known threshold variance. A second plurality of measurements of the level of the liquid in the container is then taken;

a second variance of the second plurality of measurements is calculated; and the second calculated variance is compared with a known threshold variance. The above described actions are repeated at incrementally increased back pressures until the first and second calculated variances are each greater than or equal to the known threshold variance, e.g., about 0.01 in some embodiments. The bubble point is determined to be the back pressure at that point.

In another embodiment, a method of forming cell blocks include calibrating a bubble point of a filter and liquid combination as described above, calculating an appropriate back pressure based on the bubble point, and intermittently applying the appropriate back pressure to the filter to increase flow of the sample liquid during cell block formation.

In still another embodiment, a method of identifying an unsuitable filter during formation of a cell block includes calibrating a bubble point of a filter and liquid combination; comparing the calibrated bubble point with a known threshold bubble point; and identifying the unsuitable filter when the determined bubble point is less than or equal to the known threshold bubble point, which is about 0.8 pounds per square inch. The identifying of an unsuitable filter during formation of a cell block may also include halting the formation of a cell block when an unsuitable filter is identified.

Other and further aspects and embodiments of the disclosed inventions are described in the detailed description of the accompanying drawings.

BRIEF DESCRIPTION OF THE DRAWINGS

It will be appreciated that the system and apparatus shown in the drawings are not necessarily drawn to scale, with emphasis instead being placed on illustrating the various aspects and features of the illustrated embodiments, in which.

DETAILED DESCRIPTION OF THE ILLUSTRATED EMBODIMENTS

Methods and apparatus embodying the present invention provide automated calibration of filters by determining a bubble point of a filter and sample liquid combination through analysis of the variance of a series of liquid level determinations while incrementally increasing the back pressure.

Figure 1:
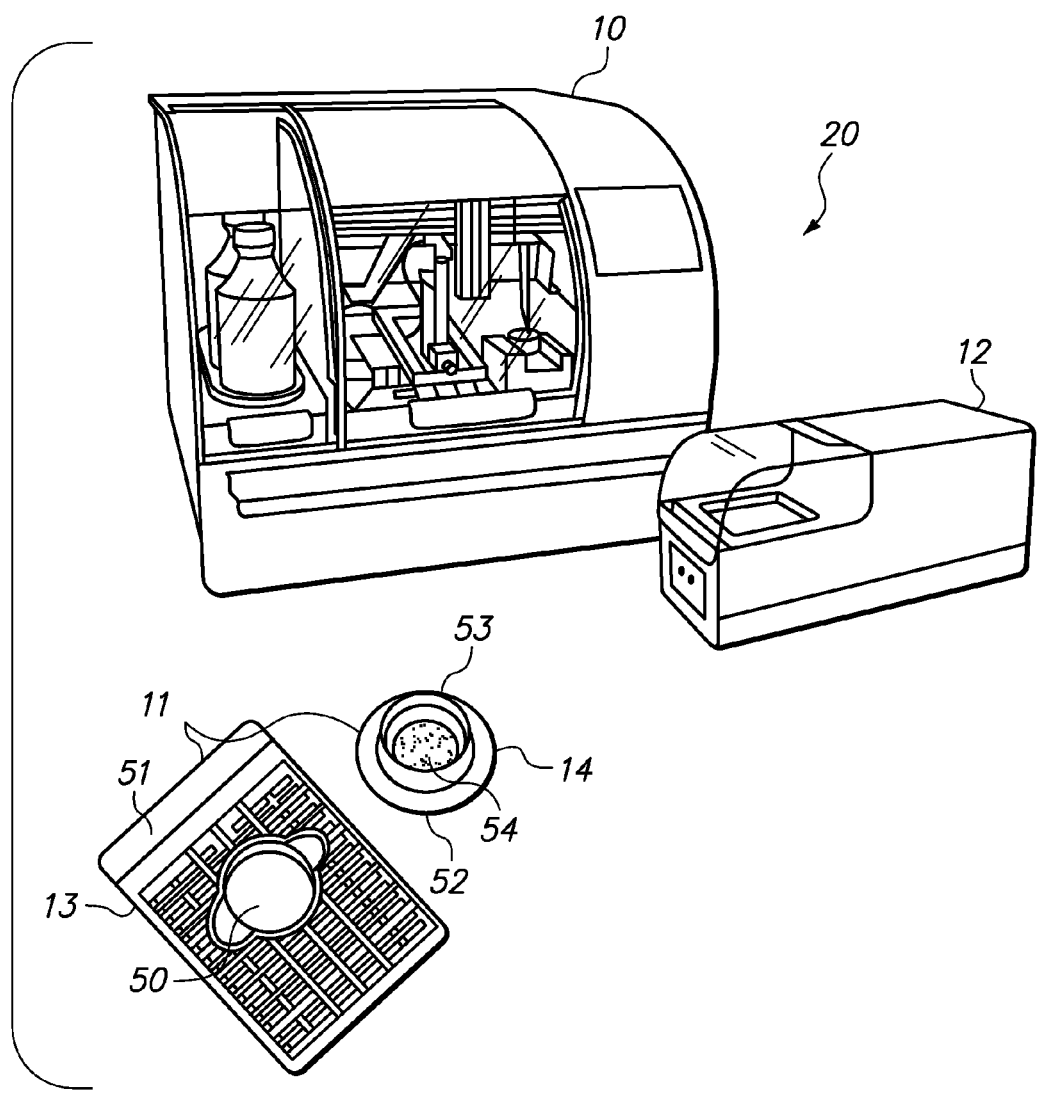
FIG. 1 is a perspective view of a cell block processing station, a cell block cassette with detachable filter, and a finishing station.

FIG. 1. depicts the main components of an exemplary cell block processing station (20), including a cell block processing station (10), a two-piece cell block cassette (11) (including a main cassette body (13) and a detachable filter assembly (14)) which captures the cellular material and guides infusion of reagents and paraffin, and a finishing station (12) for encapsulating a newly created cell block in additional paraffin in preparation for later cutting and slide preparation. The cell block process is described in great detail in the above-incorporated '531 application.

Figure 2:
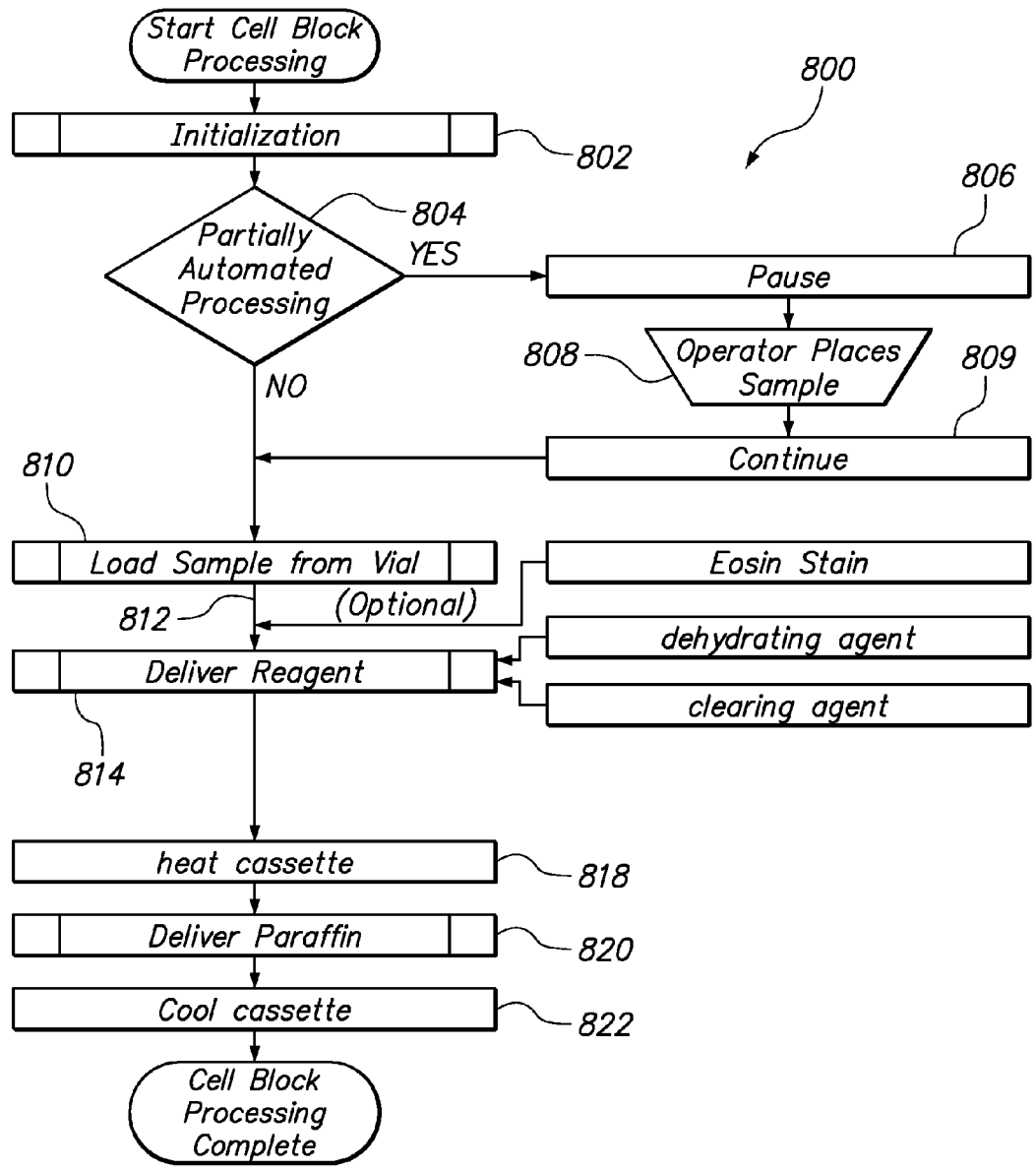
FIG. 2 is a flow chart of the process the cell block processing station undertakes to create a new cell block.
Figure 3:
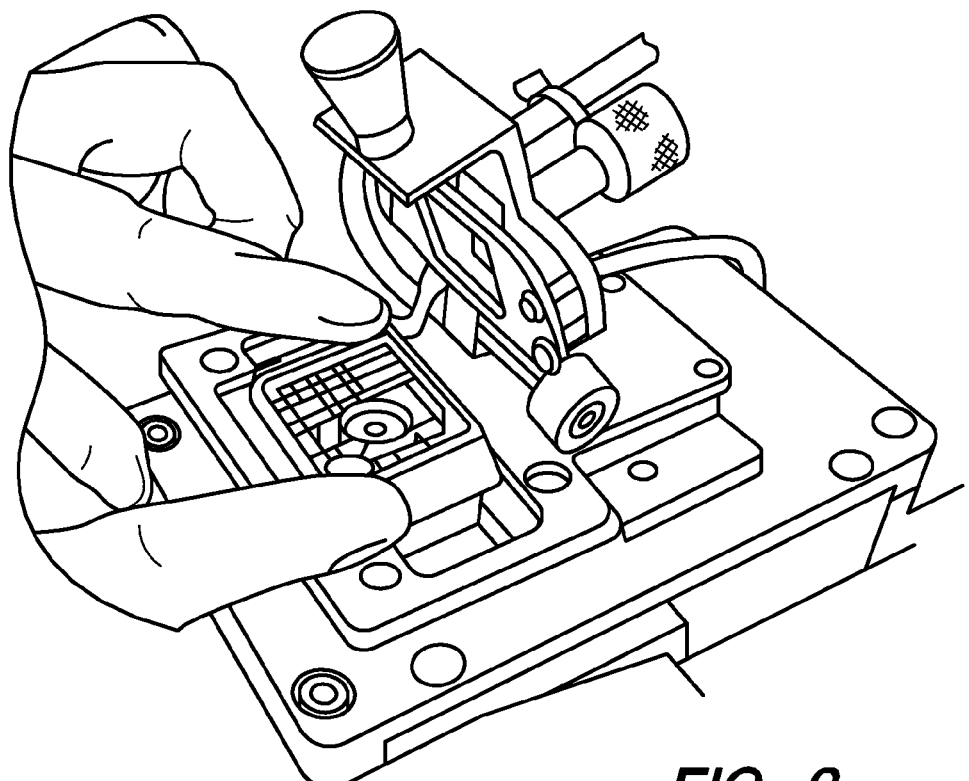
FIGS. 3 and 4 depict a user loading a cell block cassette and attached filter assembly into the cell block interface prior to creation of a new cell block.
Figure 4:
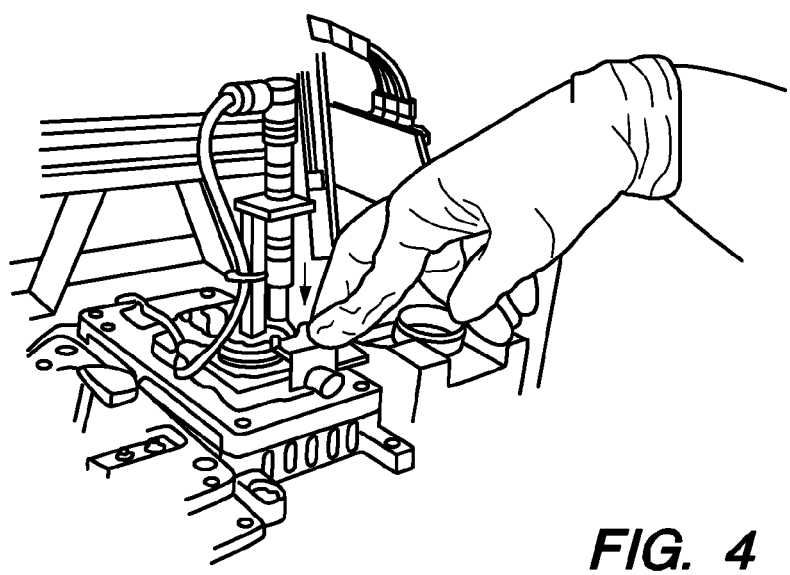

FIG. 2 is a flow chart of a cell block process 800 using a cell block processing station (20). The user has already loaded a new (and sterile) cell block cassette and filter assembly into the cassette interface of the processing station (FIGS. 3 and 4), with the sealing surface of the filter assembly forming a vacuum seal with the interior of the waste chamber. The user has also verified that there is adequate paraffin in the heated wax bath, and sterile pipette tips available at the respective sample interface and wax bath. The amount of sample fluid that is used for processing a cell block is normally limited to 20 ml, but less may be used if a sufficient cell layer is collected by the filter using less sample fluid. Thus, a user should verify that the sample vial has at least 20 ml of fluid prior to commencing the cell block process 800.

Figure 5:
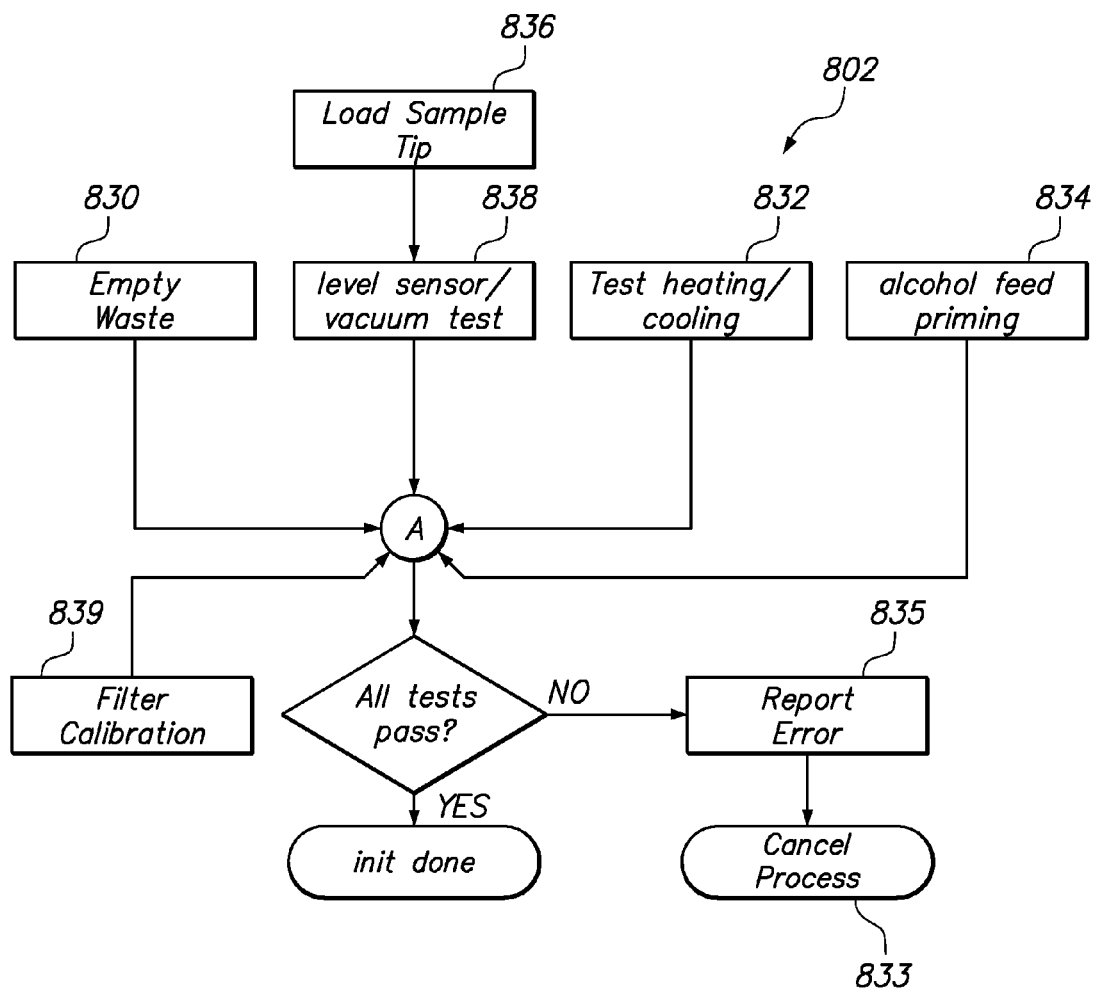
FIG. 5 is a flow chart of the system initialization process for the cell block processing station when undertaking to create a new cell block.

The cell block process 800 starts with an system initialization cycle 802 of the processing station, which (referring also to FIG. 5) includes evacuating the waste chamber (830) any liquid or solid waste remaining from prior cell block processes by opening a heated waste chamber evacuation valve; testing the heating/cooling system (832) for the sample collection well (i.e., the peltier system that controllably heats and cools, respectively, the filter support, which in turn heats or cools the contents of the collection well); and priming the isopropyl alcohol feed line (834) using the liquid waste port provided at the sample vial interface to dispose of the alcohol. The system then loads a sample fluid pipette tip (836) and tests the fluid level sensor and waste chamber vacuum systems (838). The system then calibrates the filter (839) by determining its bubble point.

Figure 6:
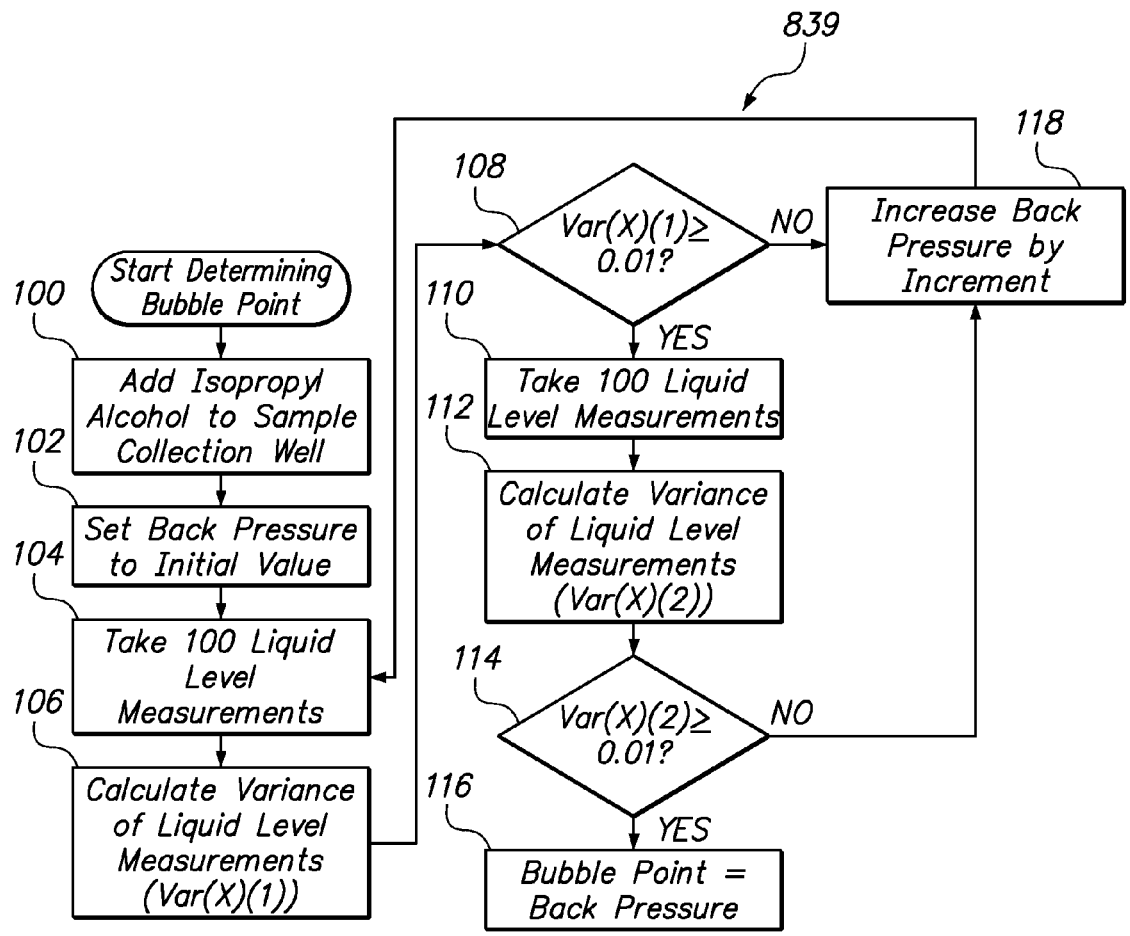
FIG. 6 is a flow chart of the bubble point determination process for the cell block processing station when undertaking to create a new cell block.

As shown in FIG. 6, the system initiates filter calibration (839) by adding one ml of isopropyl alcohol to the sample collection well (100). A small amount of vacuum is applied to the waste chamber in a quick burst to wet the filter and ensure that substantially all of the pores of the filter are full of isopropyl alcohol. The back pressure is then applied at an initial value of 0.8 pounds per square inch ("psi") (102) and the liquid level in the sample collection well is measured with an ultrasonic liquid level sensor (104). Examples of commercially available ultrasonic liquid level sensors include the Baumer UNAM 12U9914/S14D and the Baumer UNAM 12P1914/S14D. In the illustrated embodiment, one hundred liquid level measurements are taken at a rate of approximately one hundred measurements per second (104).

The variance of this set of measurements (Var(X)(1)) is calculated using the following formula: $Var(X)=E[(X-\mu)^2]$ (106). The variance when the back pressure is insufficient to form bubbles and the liquid level is at a steady state is less than 0.0005. If Var(X)(1) equals or exceeds 0.01, another set of 100 liquid level measurements is taken (108 and 110), and the variance of that second set (Var(X)(2)) is calculated as described above (112). If Var(X)(2) also equals or exceeds 0.01, then the back pressure at which these sets of liquid level measurements were taken is determined to be the bubble point (114 and 116).

If either Var(X)(1) or Var(X)(2) is less than 0.01, the back pressure is increased by 0.1 psi (108, 114, and 118), another set of one hundred liquid level measurements are taken (104), and a bubble point determination is made as described above (104-118). This process is repeated until the variances of each of two consecutive sets of one hundred liquid level measurements is equal to or greater than 0.01, and a bubble point has been determined (116).

The bubble point is utilized later in the cell block process to calibrate the back pressure needed to dislodge cellular material that is impeding flow across the filter without ejecting the material from the sample well of the cassette. Because the bubble point of a filter and liquid combination is a function of the surface tension of a liquid, one of skill in the art will recognize that once the bubble point of a filter and isopropyl alcohol is known, the bubble point of that same filter and any liquid can be derived by linear scaling. For example, for the sample liquid used in the Cellient™ Automated Cell Block System, the appropriate process back pressure is approximately 1.5 times the bubble point of the filter and isopropyl alcohol combination.

If a determined bubbled point for a filter and isopropyl alcohol combination is less than or equal to 0.8 psi the system generates an error message indicating that the filter is unsuitable for use, because it is "out of spec" (e.g., containing oversized pores), or is otherwise compromised (e.g., breached). The error message halts the cell block process and the filter should be replaced before valuable sample is lost.

Assuming no errors are encountered during the initialization process 802, the initialization is completed and the sample fluid aspiration process commences and proceeds as described in the above-incorporated '531 application. If one or more errors occur during the initialization, the system reports these to the user (835) and the cell block process is cancelled (833). The filter calibration (839) is repeated for each new filter to account for variations in pore size of different filters.

The invention may be embodied in other specific forms besides and beyond those described herein. The foregoing embodiments are therefore to be considered in all respects illustrative rather than limiting.

What is claimed is:

1. A method of calibrating a bubble point of a filter and liquid combination, comprising:
    (a) dispensing the liquid into a container, wherein the filter forms a surface of the container in contact with the liquid;
    (b) applying an initial back pressure through the filter toward the liquid;
    (c) taking a first plurality of measurements of a level of the liquid in the container;
    (d) calculating a first variance of the first plurality of measurements;
    (e) comparing the calculated first variance of the first plurality of measurements with a known threshold variance;
    (f) taking a second plurality of measurements of a level of the liquid in the container;
    (g) calculating a second variance of the second plurality of measurements;
    (h) comparing the calculated second variance of the second plurality of measurements with the known threshold variance;
    (i) incrementally increasing the applied back pressure;
    (j) repeating steps (c) to (i) until the calculated first and second variances are each greater than or equal to the known threshold variance; and
    (k) identifying the bubble point as the back pressure when the calculated first and second variances are each greater than or equal to the known threshold variance.

2. The method of claim 1, wherein dispensing the liquid into the container comprises dispensing about 1 ml of isopropyl alcohol into the container.

3. The method of claim 1, wherein the initial back pressure is about 0.8 psi.

4. The method of claim 1, wherein the known threshold variance is about 0.01.

5. The method of claim 1, wherein incrementally increasing the applied back pressure comprises increasing the applied back pressure by about 0.1 psi.

6. A method of forming a cell block, comprising:
    calibrating a bubble point of a filter and liquid combination according to the method of claim 1;
    calculating an appropriate back pressure based on the calculated bubble point;
    dispensing a sample liquid across a filter seated in a filter assembly coupled to a cell block cassette until a desired amount of cellular material carried in the sample liquid is retained by the filter;
    intermittently applying the appropriate back pressure to the filter to increase flow of the sample liquid;
    dispensing liquefied paraffin onto the filter; and
    allowing the paraffin to solidify to thereby form a substantially solid block of paraffin with the retained cellular material embedded at one end of the paraffin block against the filter.

7. A method of identifying an unsuitable filter during formation of a cell block, comprising:
    calibrating a bubble point of a filter and liquid combination according to the method of claim 1;
    comparing the calibrated bubble point with a known threshold bubble point; and
    identifying the unsuitable filter when the determined bubble point is less than or equal to the known threshold bubble point.

8. The method of claim 7, wherein the known threshold bubble point is 0.8 pounds per square inch.

9. The method of claim 7, further comprising halting the formation of a cell block when an unsuitable filter is identified.

* * * * *